US00PP18633P2

(12) United States Plant Patent
Hooijman

(10) Patent No.: US PP18,633 P2
(45) Date of Patent: Mar. 18, 2008

(54) ***TRACHELIUM* PLANT NAMED 'ESM TON'**

(50) Latin Name: *Trachelium caeruleum*
Varietal Denomination: Esm Ton

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 39 days.

(21) Appl. No.: 11/489,168

(22) Filed: Jul. 19, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Trachelium* plant named 'Esm Ton', characterized by its erect flowering stems; vigorous growth habit; numerous small green-colored flower buds that do not open; and good postproduction longevity.

1 Drawing Sheet

Botanical designation: *Trachelium caeruleum.*
Cultivar denomination: 'ESM TON'.

BACKGROUND OF THE INVENTION

The present invention relates to a new and distinct cultivar of *Trachelium* plant, botanically known as *Trachelium caeruleum,* grown commercially as a cut flower, and hereinafter referred to by the name 'Esm Ton'.

The new *Trachelium* is a product of a planned breeding program conducted by the Inventor in El Quinche, Pichincha, Ecuador. The objective of the breeding program is to create new uniform *Trachelium* cultivars with long and straight flowering stems.

The new *Trachelium* originated from a open-pollination in El Quinche, Pichincha, Ecuador in August, 2003 of a proprietary selection of *Trachelium caeruleum* identified as Line 2, not patented, as the female, or seed, parent with an unknown selection of *Trachelium caeruleum.* The cultivar Esm Ton was discovered and selected by the Inventor as a flowering plant from within the progeny of the stated open-pollination in a controlled environment in El Quinche, Pichincha, Ecuador.

Asexual reproduction of the new *Trachelium* by cuttings in a controlled environment in El Quinche, Pichincha, Ecuador since August, 2004, has shown that the unique features of this new *Trachelium* are stable and reproduced true to type in successive generations.

SUMMARY OF THE INVENTION

The cultivar Esm Ton has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Ton'. These characteristics in combination distinguish 'Esm Ton' as a new and distinct cultivar of *Trachelium:*

1. Erect flowering stems.
2. Vigorous growth habit.

3. Numerous small green-colored flower buds that do not open.
4. Good postproduction longevity.

In side-by-side comparisons conducted in El Quinche, Pichincha, Ecuador, plants of the new *Trachelium* differed from plants of the female parent selection in the following characteristics:

1. Plants of the new *Trachelium* were more freely flowering than plants of the female parent selection.
2. Flower buds of plants of the new *Trachelium* did not open whereas flower buds of plants of the female parent selection opened.

Plants of the new *Trachelium* can be compared to plants of the *Trachelium* cultivar White Powell, not patented. In side-by-side comparisons conducted in El Quinche, Pichincha, Ecuador, plants of the new *Trachelium* differed from plants of the cultivar White Powell in the following characteristics:

1. Plants of the new *Trachelium* were broader and had broader inflorescences than plants of the cultivar White Powell.
2. Plants of the new *Trachelium* had smaller leaves with shorter petioles than plants of the cultivar White Powell.
3. Flower buds of plants of the new *Trachelium* did not open whereas flower buds of plants of the cultivar White Powell opened.

BRIEF DESCRIPTION OF THE PHOTOGRAPHS

The accompanying photographs illustrate the overall appearance of the new *Trachelium.* These photographs show the colors as true as it is reasonably possible to obtain in colored reproductions of this type. Colors in the photographs may differ slightly from the color values cited in the detailed botanical description which accurately describe the colors of the new *Trachelium.* Clockwise from the upper left photograph: side perspective view of a typical flowering stem; close-up of a typical inflorescence; close-up comparisons of a typical inflorescence of the new *Trachelium* and the cultivar White Powell; and close-up view of upper and lower surfaces of typical leaves of 'Esm Ton'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in El Quinche, Pichincha, Ecuador in ground beds in a polyethylene-covered greenhouse and under conditions and practices which approximate those generally used in commercial cut *Trachelium* production. During the production of the plants, day temperatures ranged from 12° C. to 30° C. and night temperatures ranged from 5° C. to 11° C. Measurements and numerical values represent averages for typical five-month old flowering plants.

Botanical classification: *Trachelium caeruleum* cultivar Esm Ton.

Commercial classification: Cut flower *Trachelium.*

Parentage:

*Female, or seed, parent.*—Proprietary selection of *Trachelium caeruleum* identified as Line 2, not patented.

*Male, or pollen, parent.*—Unknown selection of *Trachelium caeruleum,* not patented.

Propagation:

*Type.*—By cuttings.

*Time to initiate roots.*—About 18 to 21 days at 17° C. to 25° C.

*Time to produce a rooted cutting.*—About six to seven weeks at 17° C. to 25° C.

*Root description.*—Fine, fibrous; 165D in color.

Plant description:

*Appearance.*—Perennial; grown as a cut flower. Erect and strong flowering stems. Freely flowering habit; numerous corymbs of flower buds that do not open. Vigorous growth habit. Single-stemmed plant.

*Plant height.*—About 90 cm.

*Plant diameter or spread.*—About 28 cm.

*Flowering stems.*—Length: About 90 cm. Diameter: About 7 mm. Internode length: About 3.1 cm. Strength: Strong. Texture: Smooth, glabrous. Color: 144B.

Foliage description:

*Arrangement.*—Alternate, simple; sessile.

*Length.*—About 10.9 cm.

*Width.*—About 3.9 cm.

*Shape.*—Lanceolate.

*Apex.*—Acute.

*Base.*—Attenuate.

*Margin.*—Serrate.

*Texture, upper and lower surfaces.*—Smooth, glabrous.

*Venation pattern.*—Pinnate.

*Color.*—Developing foliage, upper surface: 139A to 147A. Developing foliage, lower surface: 137C to 147B. Fully expanded foliage, upper surface: 147A; venation, 147D. Fully expanded foliage, lower surface: 147B; venation, 146D.

*Petiole length.*—About 2.7 cm.

*Petiole diameter.*—About 3 mm.

*Petiole color.*—137C; venation, 147D.

Flower description:

*Flower arrangement and habit.*—Corymbs with numerous flower buds that do not open. Very freely flowering, about 25,500 flower buds per flowering stem. Flower buds face mostly upright.

*Flowering response.*—In Ecuador, plants flower year round. Plants develop flower buds about 16 weeks after planting.

*Post-production longevity.*—As a cut flower, inflorescences last for about two weeks.

*Fragrance.*—None detected.

*Inflorescence height.*—About 47 cm.

*Inflorescence diameter.*—About 17 cm.

*Flower buds.*—Length: About 5 mm. Diameter: About 5 mm. Shape: Roughly spherical. Color: 144A.

*Flowers.*—Flower buds do not open and develop petals, sepals nor reproductive organs.

*Peduncles.*—Length: About 30.3 cm. Diameter: About 7 mm. Strength: Strong. Texture: Smooth, glabrous. Color: 144B.

*Pedicels.*—Length: About 1 mm. Diameter: About 0.5 mm. Strength: Strong. Angle: About 29° from vertical. Texture: Smooth, glabrous. Color: 146B.

Disease/pest resistance: Plants of the new *Trachelium* have been observed to be resistant to *Botrytis.* Plants have not been shown to be resistant to pests and other pathogens common to *Trachelium.*

Temperature tolerance: Plants of the new *Trachelium* have been observed to tolerate temperatures ranging from about 5° C. to about 30° C.

It is claimed:

1. A new and distinct *Trachelium* plant named 'Esm Ton' as illustrated and described.

* * * * *

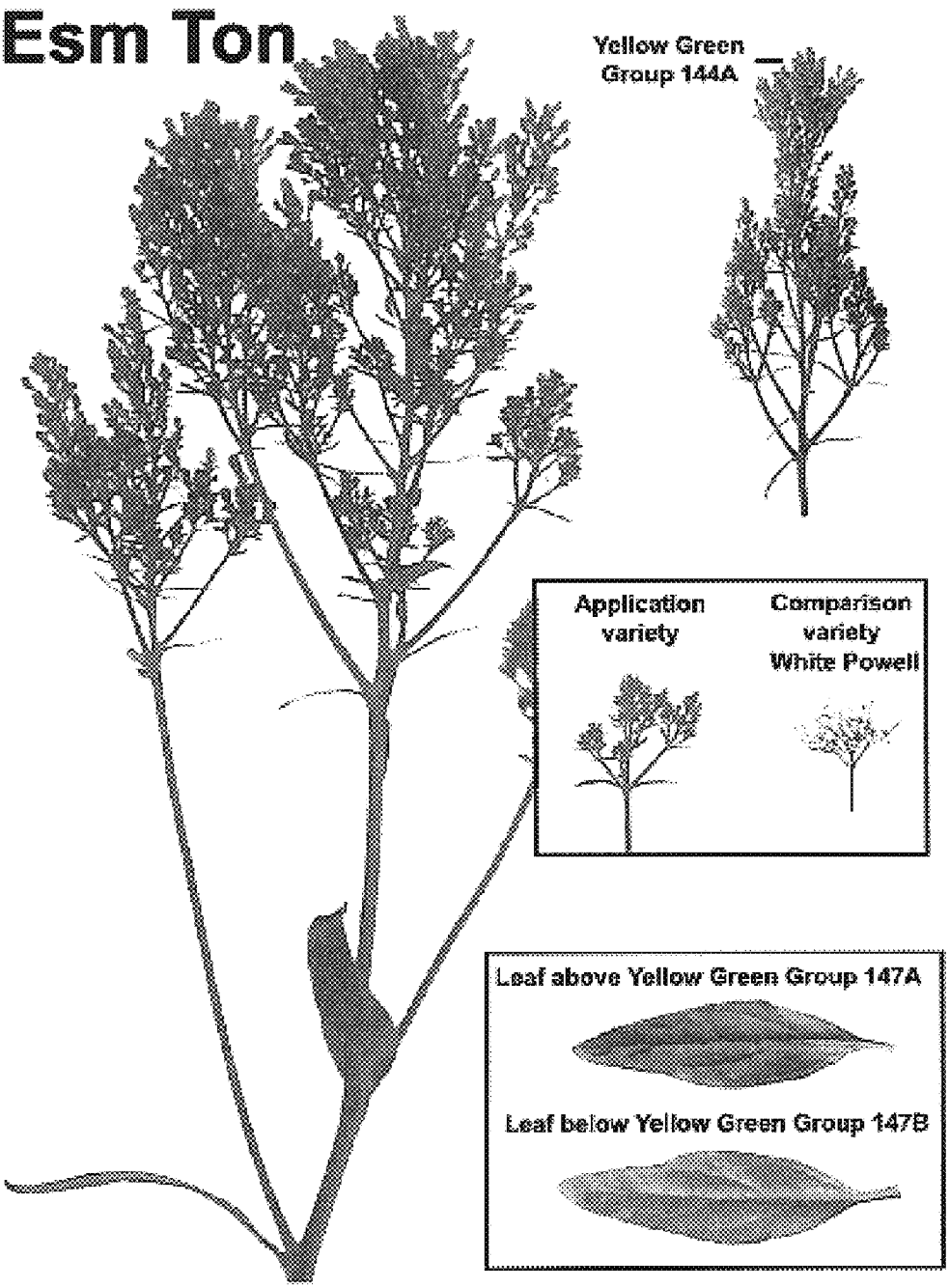
Esm Ton
Yellow Green Group 144A
Application variety
Comparison variety White Powell
Leaf above Yellow Green Group 147A
Leaf below Yellow Green Group 147B